United States Patent [19]
Tai et al.

[11] Patent Number: 5,645,544
[45] Date of Patent: Jul. 8, 1997

US005645544A

[54] VARIABLE ANGLE EXTENSION ROD

[75] Inventors: Joseph Tai; Michael C. Sherman, both of Memphis, Tenn.

[73] Assignee: Danek Medical, Inc., Memphis, Tenn.

[21] Appl. No.: 527,410

[22] Filed: Sep. 13, 1995

[51] Int. Cl.⁶ .................................................. A61B 17/56
[52] U.S. Cl. ............................ 606/61; 606/71; 606/73
[58] Field of Search ........................... 606/66, 61, 72, 606/73, 69, 76, 71

[56] References Cited

U.S. PATENT DOCUMENTS

| 4,771,767 | 9/1988 | Steffee | 128/69 |
| 5,254,118 | 10/1993 | Mirkovic | 606/61 |
| 5,257,994 | 11/1993 | Lin | 606/61 |
| 5,261,909 | 11/1993 | Sutterlin et al. | 606/61 |
| 5,330,473 | 7/1994 | Howland | 606/61 |
| 5,437,671 | 8/1995 | Lozier et al. | 606/61 |
| 5,474,551 | 12/1995 | Finn et al. | 606/61 |
| 5,498,262 | 3/1996 | Bryan | 606/72 |

FOREIGN PATENT DOCUMENTS 3219575  1/1983  Germany .

OTHER PUBLICATIONS

*TSRH Crosslink Components* Sheet, Danek Medical, Inc. (Copyright 1990).

*Primary Examiner*—Michael Buiz
*Assistant Examiner*—Mark S. Leonardo
*Attorney, Agent, or Firm*—Woodard, Emhardt, Naughton Moriarty & McNett

[57] ABSTRACT

One embodiment of the invention a spinal fixation system includes an elongated spinal element (11) configured to extend adjacent the spine, and a plurality of fixation elements (15) each engagable to the spine and to the elongated spinal element (11). The embodiment further includes an extension member (28) having a head portion (30) defining a variable angle surface and an elongated portion (29) extending from the head portion, and a clamping member (31) for clamping the extension member (28) to the elongated spinal element (11). The clamping member (31) defines a mating surface configured for mating engagement with the variable angle surface of the extension member (28) to permit orientation of the elongated portion (29) of the extension member (28) at a plurality of angles relative to the elongated spinal element (11).

14 Claims, 5 Drawing Sheets

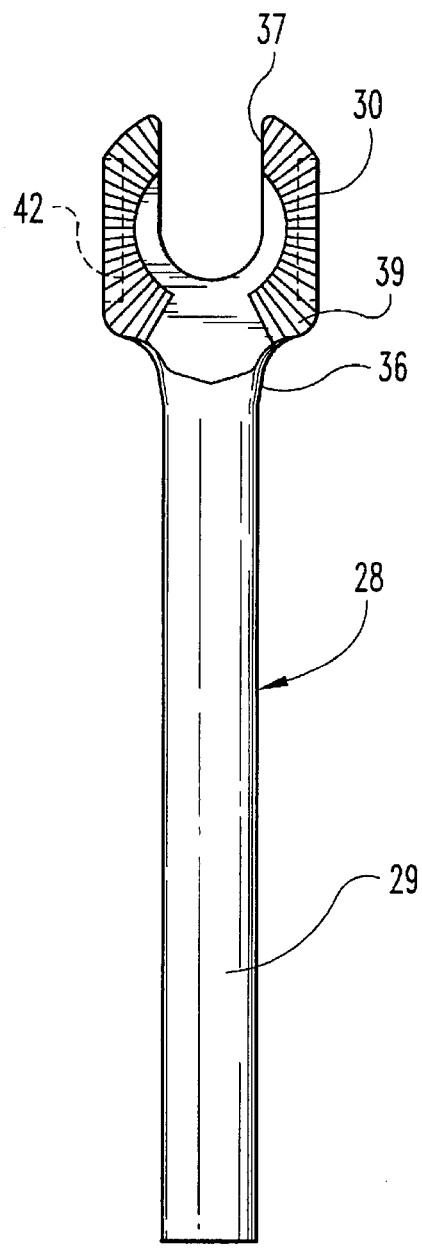
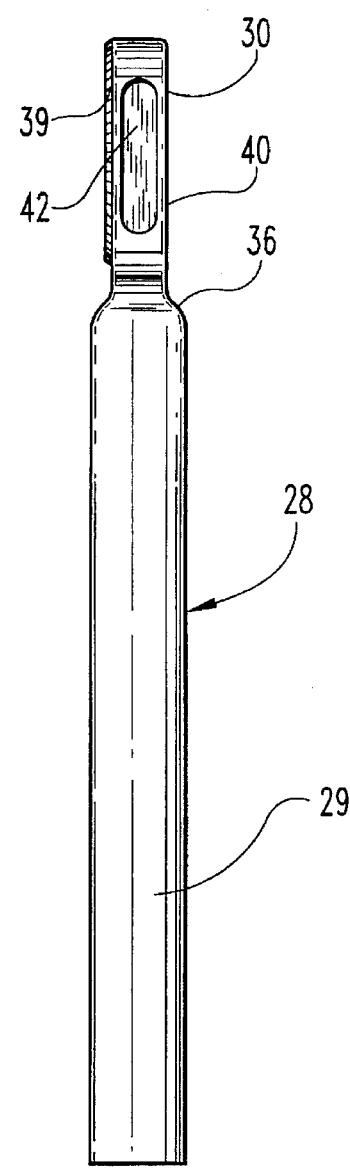
Fig. 3  Fig. 4

VARIABLE ANGLE EXTENSION ROD

BACKGROUND OF THE INVENTION

The present invention broadly concerns devices and systems for use in the fixation of the spine and correction of spinal disorders. In one aspect, the invention concerns a spinal implant system utilizing elongated fixation elements, such as spinal rods, contoured for connection at various locations along the length of the spinal column. More specifically, the invention concerns a device for connecting the spinal rod to various vertebrae or the pelvis, while permitting variation in several degrees of freedom.

Several techniques and systems have been developed for use in stabilizing spinal curves and facilitating spinal fusion to correct spinal injuries and deformities. Frequently, an elongated spinal member, such as a bendable rod, is longitudinally disposed adjacent the vertebral column. The rod is fixed to various vertebrae along the length of the column by a number of fixation elements such as hooks or bone screws of various configurations. One example is the construct depicted in FIG. 1 which uses Danek Medical Inc.'s TSRH® spinal system. The fixation system 10 includes two elongated rods 11 disposed adjacent the spine on opposite sides of the spinous process. A variety of bone engaging fasteners 15 are engaged to the rods 11 by way of eyebolt assemblies 16. These eyebolt assemblies are known components of the TSRH® system and are particularly known for the "three-point shear clamp" effect achieved by the eyebolt assemblies to clamp the bone engaging fasteners 15 to the spinal rods 11.

It is often desirable to anchor the inferior end of the construct to either the sacrum or the pelvis to increase the stability of the construct. The rods of the system shown in FIG. 1 extends from the thoracic vertebrae to the sacrum and pelvis. In some prior art systems, this anchoring required bending the inferior end of the spinal rod which unfortunately has serious disadvantages. Bending the rod complicates the surgery, causes mechanical problems, and requires a more complicated spinal rod to be implanted. The Galveston fixation technique addressed this problem by providing a bend in the spinal rod. The construct shown in FIG. 1 uses an improvement of the Galveston technique in which a short rod segment 12 having a Galveston bend 14 is axially attached to the spinal rod 11.

As shown in FIG. 1, the system 10 is anchored to the iliac wings I by a pair of Galveston rod segments 12 each linked to the inferior end 11a of the respective spinal rod 11. The Galveston rod segments 12 each include an iliac extension 13 which is engaged within holes bores through the iliac wings. The Galveston rod segments 12 are engaged to the spinal rods 11 by way of a pair of offset plates 20 and eyebolt assemblies 21. The offset plate 20 axially links each Galveston rod segment 12 to the respective spinal rod 11. A transverse plate 17, preferably the Crosslink® plate provided by Danek Medical, is engaged between the two Galveston rod segments 12 by way of separate eyebolt assemblies 18. The addition of the Crosslink® transverse plate 17 adds greater strength and rigidity to the construct and prevents pullout of the iliac extensions 13 from the iliac wings I. This technique allows the substitution of a much shorter rod segment 12 already carrying the Galveston bend, thereby permitting ready engagement between the iliac wings and the spinal rods 11.

Although the use of the offset plates 20 has greatly simplified fixation in anchoring to the iliac bone from the prior Galveston technique, there still is room for improvement. In particular, rod bending is still required to create the iliac extensions 13. It is a known principal of mechanical engineering that bends in the rods yield stress concentrations and can also produce assymetric loading of the fixation construct. Moreover, the tools used to bend the rods can create notches in the rods which may compromise the overall strength of the construct.

It is therefore desirable to engage the bones of the sacrum or ilium without bending spinal rods. Custom fit capabilities such as angular and translational adjustability are also desirable. It is further desirable to provide such devices which can be readily connected to existing spinal fixation systems.

SUMMARY OF THE INVENTION

In order to address these needs, a spinal fixation system is presented comprising an elongated spinal element, such as a rod, configured to extend adjacent the spine. The rod is engaged to several vertebrae along the spine by way of a plurality of fixation elements. Each of these fixation elements is connected to a spinal rod by way of engaging means, most preferably in the form of eyebolt assemblies.

The inventive fixation system further includes an extension member having a head portion configured for engagement to the spinal rods, and an elongated portion, preferably in the form of a rod, integrally extending therefrom. The elongated portion is adapted to receive one of the plurality of fixation elements to engage the extension member to the bones of the spine or ilium. The system further includes a clamping member for clamping the extension member to the elongated spinal rod. In an important aspect of the invention, the head portion of the extension member and the clamping member include corresponding surfaces which are configured to permit engagement between the two components at variable angles relative to each other. In one specific embodiment, the head portion of the extension member and the mating surface of the clamping member include a plurality of interdigitating radial splines.

In a further aspect of the invention, the clamping member can include an eyebolt assembly which engages the spinal rod. The eyebolt assembly includes an eyebolt body defining an aperture for receiving the spinal rod therethrough, and a threaded stem extending from the body. A threaded nut is arranged to engage the threaded stem. A washer is also provided which defines an opening for receiving the threaded stem of the eyebolt therethrough. The washer also includes a contact surface for contacting the spinal rod which preferably includes a groove sized to receive the rod. The opposite surface of the washer corresponds to the mating surface bearing the interdigitating radial splines. In the assembly of the extension member, the eyebolt is positioned on the spinal rod, the washer is disposed over the threaded stem of the eyebolt and having its groove in contact with the spinal rod, the splined head portion of the extension member is disposed over the eyebolt stem and in interdigitating contact with the washer, and the nut is then tightened onto the threaded stem to clamp the construct together.

In one preferred embodiment, the extension rod assembly is engaged to the inferior end of a spinal rod construct and spans between the spinal rod and the iliac wings. In a further embodiment, the extension rod assembly is used to provide a lateral extension from the spinal rod for engaging a fixation element, such as a bone screw, to the sacrum or to other vertebral bodies.

One advantage of the present invention resides in features that permit several degrees of variability of the extension rod assembly relative to the spinal rods. In particular, the use of the clamping member allows the extension rod assembly to slide or translate longitudinally along the length of the spinal rod. Further, the use of the eyebolt in the clamping member allows the extension rod assembly to rotate about the longitudinal axis of the spinal rod.

Another advantage of this invention is that it allows engagement of a spinal fixation system construct to the sacrum or the ilium without bending the inferior ends of the spinal rods. This feature avoids the resulting mechanical and surgical problems. Finally, the interdigitating feature of the clamping member allows the longitudinal axis of the extension rod assembly to assume variable angular orientations relative to the longitudinal axis of the spinal rod.

It is one object of the present invention to provide a variable angle rod extension that can be engaged to an existing spinal rod construct to fasten additional bone engaging fasteners to the spinal rod. Another object is to provide a rod extension which can assume variable angular orientations in at least two angular degrees of freedom with respect to the spinal rod.

A further object of the invention is to provide a rod extension which also permits translational adjustment along the length of a spinal rod construct. An additional object resides in aspects of the invention that permit top-tightening of the variable angle rod extension to the existing spinal rod construct. Other objects, advantages and benefits of the present invention will become apparent upon consideration of the following description of the preferred embodiments together with the accompanying figures.

DESCRIPTION OF THE DRAWINGS

FIG. 3 is a top elevational view of an extension rod used with the variable angle extension rod assembly shown in FIG. 2.

FIG. 4 is a side elevational view of the extension rod shown in FIG. 3.

DESCRIPTION OF THE PREFERRED EMBODIMENT

Figure 1:
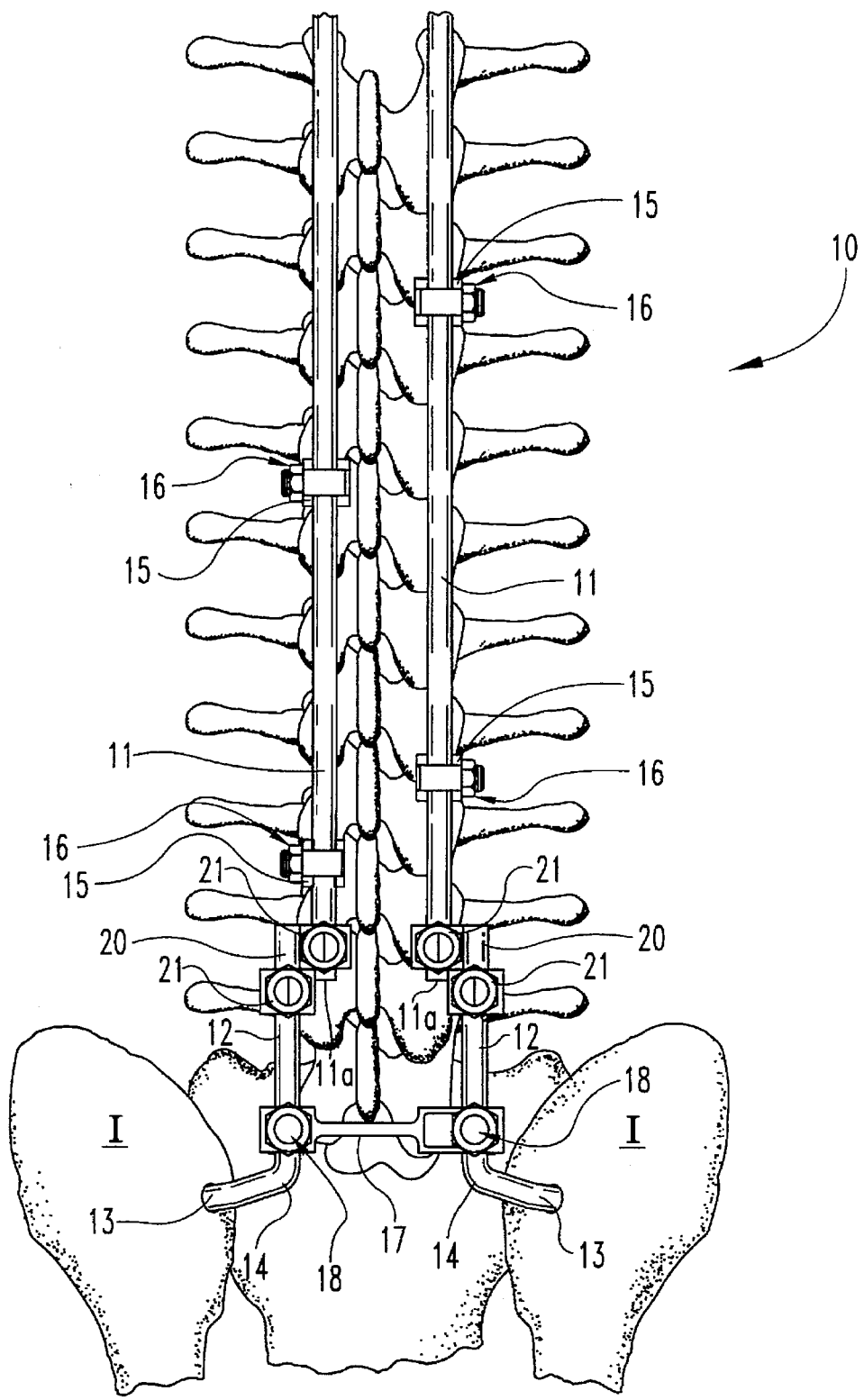
FIG. 1 is a top elevational view of a spinal fixation construct in accordance with one prior art system.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention concerns orthopedic devices and systems which provide stable constructs without the mechanical disadvantages of prior art systems which require bent rods. The invention is beneficial in that it provides stable constructs by allowing attachment of spinal rods both along the spine and to the pelvis without the requirement of bending the inferior ends of the rods. The devices also provide angular and translational adjustability for a custom fit for each patient. The devices of this invention are readily top loaded to existing spinal systems.

Figure 2:
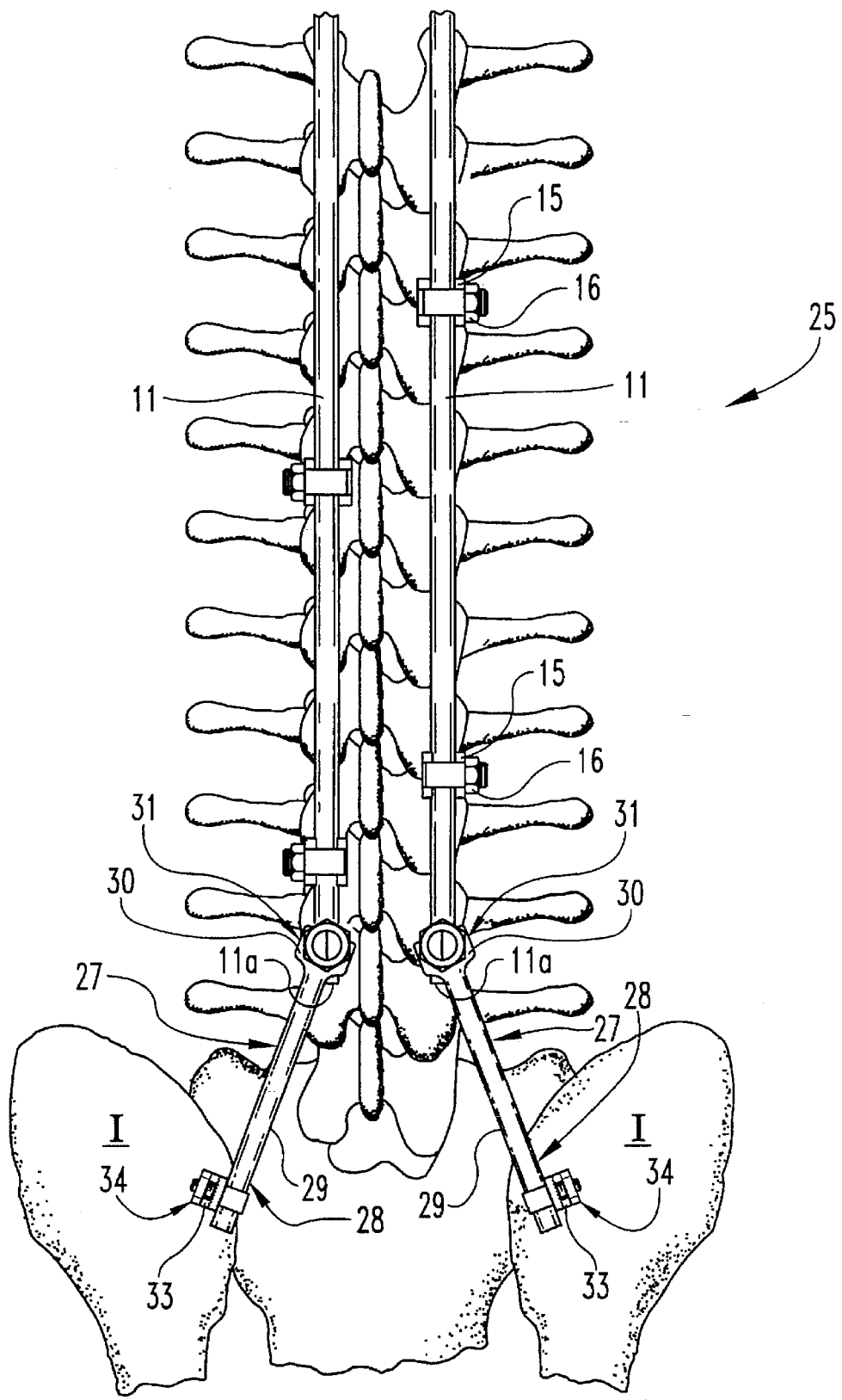
FIG. 2 is a top elevational view of a spinal fixation system utilizing a variable angle extension rod assembly in accordance with one embodiment of the present invention.

Referring to FIG. 2, one preferred embodiment of the present invention is depicted. Specifically, a spinal fixation system is shown which utilizes a pair of elongated spinal elements, such as rods 11, configured to be disposed adjacent and along the length of the spine. It is of course known that the spinal rods 11 can extend over several vertebral levels and can terminate at any of several locations along the spine. For purposes of illustration, the spinal rods 11 in this fixation system 25 are shown with their inferior ends adjacent the lower lumbar vertebrae. As with the prior art systems, the spinal rods 11 of fixation system 25 are engaged to various vertebrae by way of bone engaging fasteners 15 attached to the spinal rods by way of eyebolt assemblies 16. The bone engaging fasteners 15 can be any suitable fastener, such as laminar or pedicle hooks or bone screws of known design.

The inventive fixation system 25 includes an extension rod assembly 27 engagable to the inferior end 11a of the spinal rods 11. The extension rod assembly 27 includes an extension rod 28, a clamping member 31, and a bone engaging fastener, which is engagable to the iliac wings I. The bone engaging fastener is preferably of the type of the bone screw 33 shown in FIG. 2. The extension rod 28 includes an elongated rod portion 29 and a head portion 30. The clamping member 31 is used to connect or clamp the head portion 30 of the extension rod 28 to the corresponding spinal rods 11.

The extension rod 28, and particularly the elongated rod portion 29, is configured to receive a clamping member 31 for attaching the bone screw 33 to the extension rod 28. In the preferred embodiment, this clamping member is an eyebolt assembly 33, again of known design, which permits ready connection of the head of the bone screw 33 to the extension rod 28.

Referring to FIGS. 3 and 4, details of the extension rod 28 are shown. As mentioned above, the extension rod 28 includes an elongated rod portion 29 and a head portion 30. Preferably, the rod portion 29 is cylindrical and has substantially the same diameter as the spinal rods 11. The elongated rod portion 29 blends into the head portion 30 at a transition region 36.

As shown more clearly in FIG. 4, the head portion 30 preferably includes opposite flat surfaces 39 and 40. As shown in FIG. 3, the head portion 30 preferably includes a slot 37 open at the top of the head portion. This slot 37 allows engagement of the extension rod by way of the clamping member 31 as described more fully below. The head portion 30 also preferably includes a surface feature which permits variable angular orientations between the clamping member and the extension rod. Most preferably, the head portion includes a radially splined surface 39. As shown in FIG. 3, the radial splines preferably do not occupy the entire face of the head portion 30, although longer radial splines can be contemplated. The head portion 30 includes an opposite surface 40, which is preferably smooth. The head portion 30 also includes holding instrument recesses 42 defined in opposite sides of the head portion. The recesses 42 are configured to be engaged by typical holding instruments, such as instruments used to hold spinal hooks or bone screws for implantation adjacent the spine. The same instruments can be used to hold the extension rod 28 when adding the rod to a spinal fixation construct.

Figure 6:
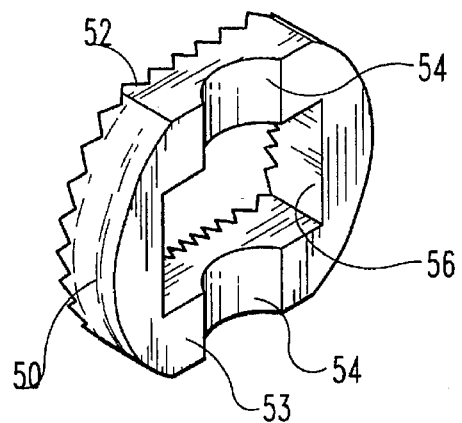
FIG. 6 is an enlarged perspective view showing a washer used with the clamping member depicted in FIG. 5.
Figure 5:
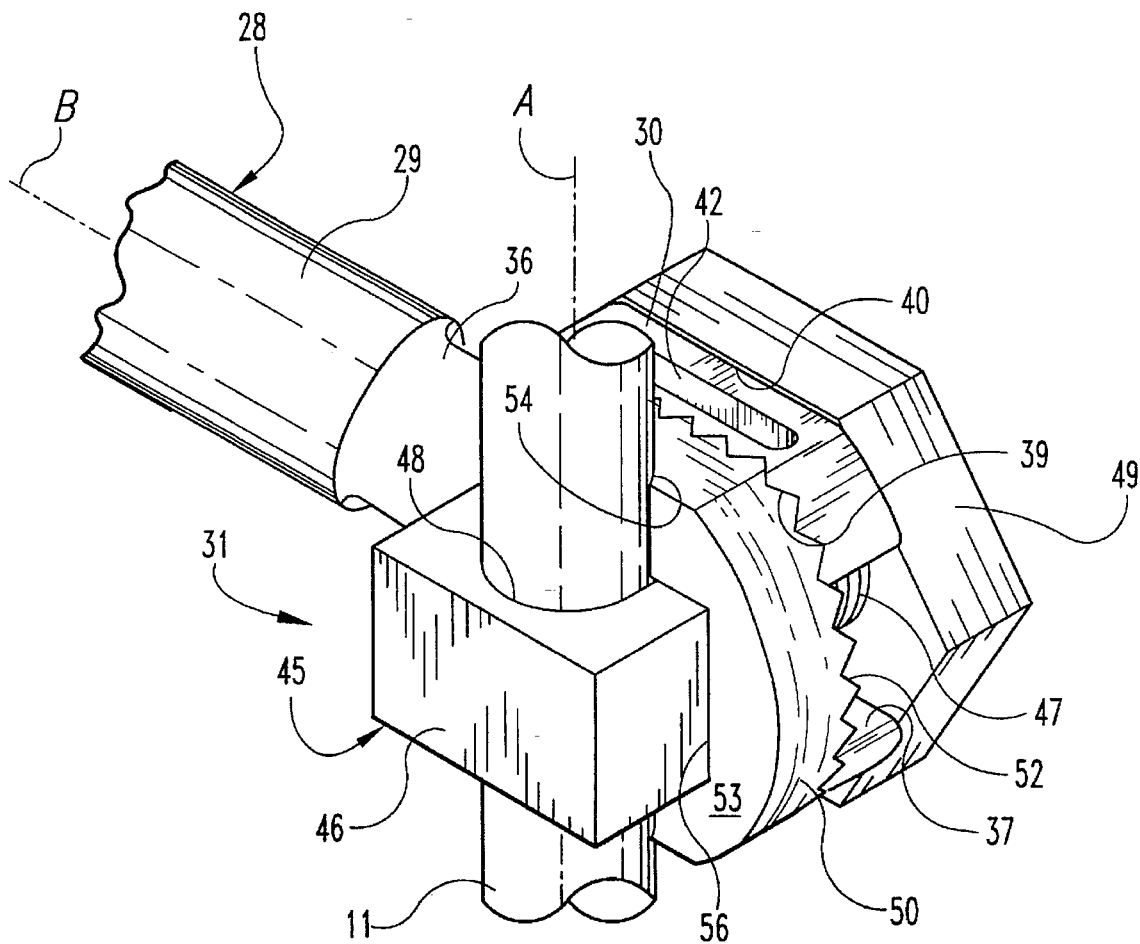
FIG. 5 is an enlarged detailed perspective view showing a clamping member and the extension rod of the variable angle extension rod assembly shown in FIG. 2.

Referring now to FIGS. 5 and 6, details of the clamping member 31 according to one embodiment and the manner in which it connects the extension rod 28 to the spinal rod 11 are shown. The clamping member 31 preferably includes an eyebolt 45 having a body 46 and a threaded stem 47 projecting from the body. A threaded nut 49 is configured to engage the threaded stem. In accordance with its known construction, the eyebolt body 46 also includes an aperture 48 through which the spinal rod 11 extends.

In a further aspect of the clamping member 31, a mating surface 52 is provided which mates with the surface 39 of the extension rod. Preferably, the mating surface is provided on a washer 50 that is disposed between the spinal rod 11 and the head portion 30 of the extension rod 28. Also preferably, the washer mating surface 52 is correspondingly splined so that the splines between the washer and the extension rod head portion 30 interdigitate. This interdigitation permits variable angular orientations of the head portion 30 relative to the washer 50.

The washer 50 also preferably includes an opposite rod contact surface 53 which defines a groove 54. The groove has a diameter that will receive the spinal rod 11 therein. Preferably in accordance with the TSRH® three point shear clamp philosophy, the groove 54 has a radius slightly smaller than the radius of the spinal rod 11. The washer 50 further includes an eyebolt opening 56 which is configured to fit over the body 46 of the eyebolt 45. In the preferred embodiment, the eyebolt body 46 is rectangular, so that the eyebolt opening 56 is also rectangular.

The manner in which the extension rod 28 is engaged to the spinal rod 11 by the clamping member 31 can be discerned from FIG. 5. Preferably, the eyebolt 45 is first disposed on the spinal rod 11 with its threaded stem projecting upward (see FIG. 2). The washer 50 is then placed over the threaded stem 47 with the eyebolt body 46 positioned firmly within the eyebolt opening 56. The washer 50 is situated with the groove 54 contacting the spinal rod 11 and the splined mating surface 52 facing upward. At this point, the extension rod 28 is added to the construct with the radial splined surface 39 interdigitating with the mating surface 52 of the washer.

The nut 49 is then loosely threaded onto the threaded stem 47 of the eyebolt so that the nut 49 contacts the opposite surface 40 of the head portion 30 of the extension rod 28. With the nut 49 loosely threaded onto the stem 47, the angle between the extension rod 28 and the washer 50 can be adjusted. More specifically, the angle between the longitudinal axis A of the spinal rod 11 and the longitudinal axis B of the extension rod 28 can be adjusted. In FIG. 5, this angle between the two longitudinal axes A, B is roughly 90°. On the other hand, the angle between these longitudinal axes of the construct shown in FIG. 2 is closer to 180°.

It can also be seen from FIG. 5 that until the nut 49 is fully tightened, the eyebolt 45 may freely rotate about the longitudinal axis A of the spinal rod 11. Likewise, the eyebolt 45 may freely translate along the length of the spinal rod parallel to the longitudinal axis A. Thus, it can be seen that the extension rod assembly 27, by way of the clamping member 31, is capable of adjustment in two angular degrees of freedom and one linear degree of freedom. This degree of adjustment is much greater than that which has been available with prior art systems and allows the surgeon to have greater flexibility in the placement of bone engaging fasteners, such as bone screws 33. This variable angle capability and adjustability also avoids the need to bend the rod as was typical in the prior Galveston techniques.

Figure 7:
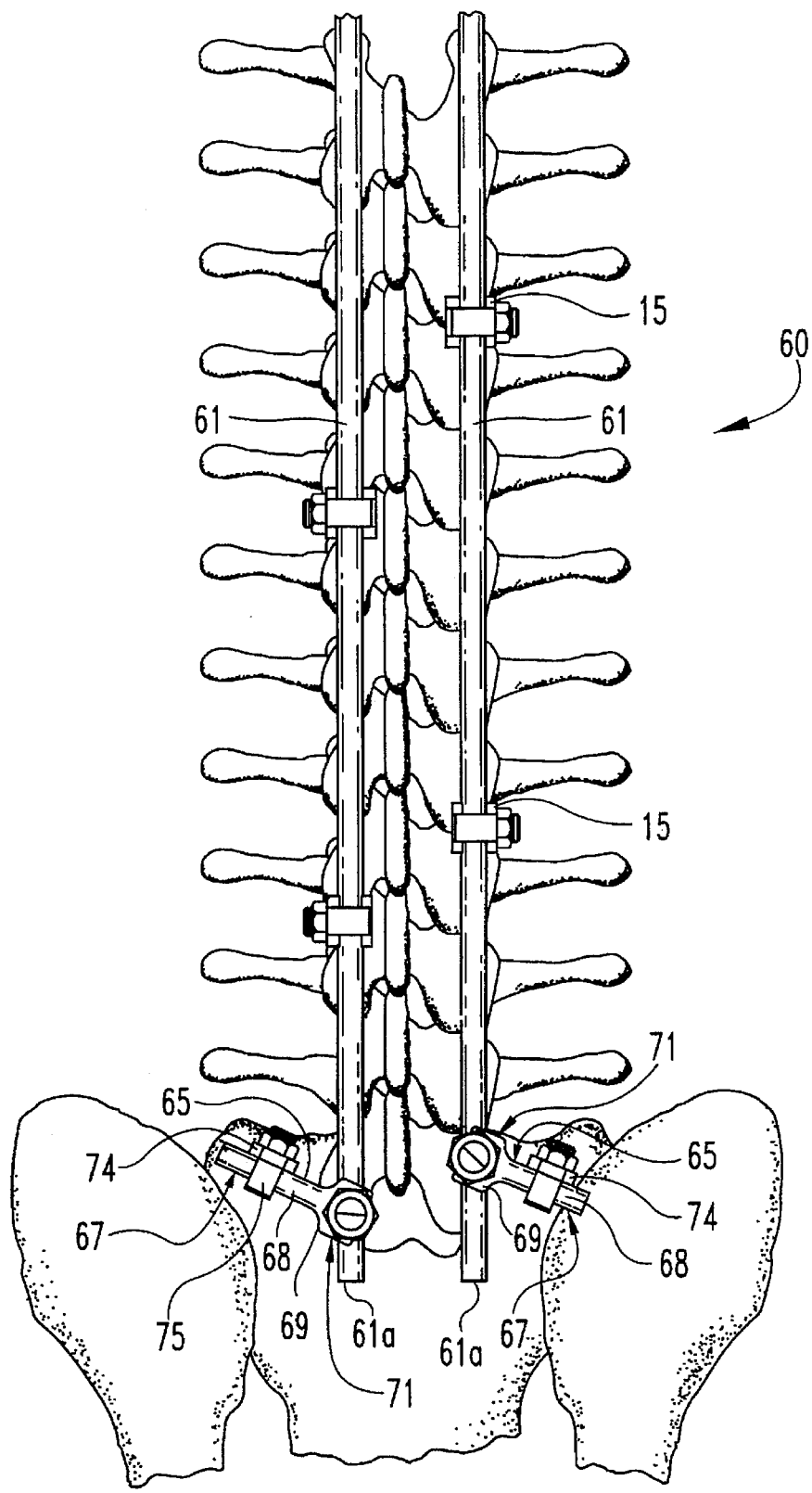
FIG. 7 is a top elevational view showing a further embodiment of the invention in which an extension rod assembly is used to provide lateral offset connection for a bone engaging fastener to a spinal rod.

In another embodiment of the invention shown in FIG. 7, a spinal fixation system 60 is shown having a pair of elongated spinal rods 61 similar to those shown in FIGS. 1 and 2. In this instance the spinal rods are longer, with inferior ends 61a adjacent the sacrum. In this embodiment, the inferior ends of the construct are affixed to the sacrum by way of bone screws 74. The extension rod assemblies 65 include an extension rod 67 which is much shorter than that shown in FIG. 2. Each extension rod 67 includes a rod portion 68 and a head portion 69, all generally similar to the like components of the extension rod 28 shown in FIGS. 3–5. Likewise, the extension rod assemblies 65 include a clamping member 71 which is configured like the clamping member 31 shown in FIG. 5.

Finally, the bone screws 74 which are engaged into the sacrum can be conveniently attached to the rod portion 68 of the extension rods 67 by way of known eyebolt assemblies 75. In this embodiment, it can be seen that the extension rods 67 are much shorter and are oriented at generally 90° angles to the spinal rods 61. Again, the two angular degrees of adjustability, coupled with the linear adjustability of the extension rod assembly 65 relative to the spinal rod 61 provide greater flexibility in fixing the inferior end of the spinal fixation construct 60.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

For example, the variable angle capability of the extension rod assembly 27 can be achieved with the radial splines described above. This radial spline arrangement is also discussed more fully in U.S. Pat. No. 5,261,909 showing a variable angle screw for a spinal implant system. However, other surface features are contemplated which permit variable relative angular orientations between the clamping member and the extension rod of the extension rod assembly. For instance, certain knurling patterns can permit variable angular relationships between the two components.

The elements of the spinal fixation system according to this invention are formed of a high-strength biocompatible material, such as 316 LVM stainless steel; however, other materials such as titanium are contemplated. Each of the elements of the extension rod assembly 27 are sized according to the particular region of the spine in which their use is intended. For instance, in the lumbar region, the components can be bigger and longer, on the order three inches long and a half inch wide, with a extension rod radius of slightly less than one quarter inch. On the other hand, if the extension rod assembly is used to provide a laterel connection, as shown in FIG. 7, as opposed to an iliac connection, as shown in FIG. 2, the rod length would be much shorter. Similarly, if the extension rod assembly 27 is used in the upper vertebral regions, such as the upper thoracic and cervical vertebral regions, the components of the extension rod assembly would be correspondingly down-sized.

The systems and devices of the present invention provide stable constructs by allowing engagement of spinal rods along the spine and also to the pelvis without the mechanical and surgical disadvantages of bending rods. The angular and translational adjustability features of this invention provide a custom fit for each patient by allowing the surgeon flexibility in the placement of bone engaging fasteners. Furthermore, the devices of this invention can be readily and conveniently top loaded to existing spinal systems.

What is claimed:

1. A spinal fixation system comprising:

an elongated spinal element configured to extend adjacent the spine;

a plurality of fixation elements each having a bone engaging portion configured for engaging the spine and engaging means for engaging said fixation element to said elongated spinal element;

an extension member having a head portion and an elongated portion extending therefrom, said elongated portion configured for placement adjacent the spine and adapted to receive one of said plurality of fixation elements engaged thereon by said engaging means, and said head portion defining a variable angle surface; and a clamping member for clamping said extension member to said elongated spinal element, said clamping member having a mating surface configured for mating engagement with said variable angle surface of said extension member to permit orientation of said elongated portion of said extension member at a plurality of angles relative to said elongated spinal element.

2. The spinal fixation system according to claim 1, wherein:

said elongated spinal element is a spinal rod; and said clamping member includes;

an eyebolt defining an aperture for receiving said spinal rod therethrough and having a threaded stem extending therefrom;

a washer defining an opening for receiving said threaded stem therethrough and having said mating surface and a first surface opposite said mating surface. said first surface being configured for contacting said spinal rod when said washer is received over said threaded stem of said eyebolt and said eyebolt is disposed on said spinal rod;

a nut for threaded engagement with said threaded stem for clamping said head portion of said extension member and said washer between said nut and said spinal rod with said first surface of said washer contacting said spinal rod and said variable angle surface contacting said mating surface in mating engagement.

3. The spinal fixation system according to claim 1, wherein said variable angle surface of said extension member and said mating surface define interdigitating locking elements.

4. The spinal fixation system according to claim 3, wherein said interdigitating locking elements include interdigitating radially spaced apart splines defined on each of said variable angle surface and said mating surface.

5. The spinal fixation system according to claim 1, wherein:

said elongated spinal element is a first rod;

said elongated portion of said extension member is a second rod; and said engaging means for each of said plurality of fixation elements includes an eyebolt for clamping onto one of said first and second rods.

6. The spinal fixation system according to claim 1, wherein said elongated portion of said extension member is a generally smooth rod.

7. The spinal fixation system according to claim 1, wherein said head portion defines a slot configured to receive said clamping member.

8. An extension device for engaging an elongated spinal element engaged to and extending along the spine and the bone of the pelvis, comprising:

an extension member having a head portion defining a variable angle surface and an elongated portion extending from said head portion a fixation element having a bone engaging portion and engaging means for engaging said fixation element to said elongated portion; and a clamping member for clamping said extension member to the elongated spinal element, said clamping member having a mating surface configured for mating engagement with said variable angle surface of said extension member to permit orientation of said elongated portion of said extension member at a plurality of angles relative to said elongated spinal element.

9. The extension device according to claim 8, wherein:

said clamping member includes;

an eyebolt defining an aperture for receiving the elongated spinal element therethrough and having a threaded stem extending therefrom;

a washer defining an opening for receiving said threaded stem therethrough and having said mating surface and a first surface opposite said mating surface.

said first surface being configured for contacting the elongated spinal element when said washer is received over said threaded stem of said eyebolt and said eyebolt is disposed on the elongated spinal element; and a nut for threaded engagement with said threaded stem for clamping said head portion of said extension member and said washer between said nut and the elongated spinal element with said first surface of said washer contacting the spinal element and said variable angle surface contacting said mating surface in mating engagement.

10. The extension device according to claim 8, wherein said variable angle surface of said extension member and said mating surface define interdigitating locking elements.

11. The extension device according to claim 10, wherein said interdigitating locking elements include interdigitating radially spaced apart splines defined on each of said variable angle surface and said mating surface.

12. The extension device according to claim 8, wherein:

said engaging means for said fixation element includes an eyebolt for clamping onto said elongated portion.

13. The extension device according to claim 8, wherein said elongated portion of said extension member is a generally smooth rod.

14. The extension device according to claim 8, wherein said head portion defines a slot configured to receive said claimping member.

* * * * *